(12) United States Patent
Hadwen et al.

(10) Patent No.: US 10,571,426 B2
(45) Date of Patent: Feb. 25, 2020

(54) BIO-SENSOR PIXEL CIRCUIT WITH AMPLIFICATION

(71) Applicant: Sharp Life Science (EU) Limited, Oxford (GB)

(72) Inventors: Benjamin James Hadwen, Oxford (GB); Campbell Donald Brown, Oxford (GB); Christopher James Brown, Oxford (GB); Gregory Gay, Oxford (GB); Sally Anderson, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 79 days.

(21) Appl. No.: 16/101,915

(22) Filed: Aug. 13, 2018

(65) Prior Publication Data

US 2019/0004009 A1 Jan. 3, 2019

Related U.S. Application Data

(62) Division of application No. 15/204,359, filed on Jul. 7, 2016, now Pat. No. 10,082,481.

(51) Int. Cl.
*G01N 27/414* (2006.01)
*G01N 27/00* (2006.01)
*G01N 31/00* (2006.01)

(52) U.S. Cl.
CPC ....... *G01N 27/4145* (2013.01); *G01N 27/414* (2013.01); *G01N 27/4148* (2013.01)

(58) Field of Classification Search
CPC .... G01N 27/00; G01N 31/00; G01N 27/4145; G01N 27/414; G01N 27/4148
See application file for complete search history.

(56) References Cited

U.S. PATENT DOCUMENTS 8,247,849 B2 8/2012 Fife et al.
8,415,716 B2 4/2013 Rothberg et al.
(Continued)

OTHER PUBLICATIONS

Extended Search Report of EP Application No. 17178846.6 dated Nov. 7, 2017, 10 pages.
Jang H.-J. et al., "Sensitivity enhancement of amorphous InGaZnO thin film transistor based extended gate field-effect transistors with dual-gate operation", Sensors and Actuators B: Chemical vol. 181, May 2013, pp. 880-884 (Abstract only).
(Continued)

*Primary Examiner* — Brian J. Sines
(74) *Attorney, Agent, or Firm* — Renner, Otto, Boisselle & Sklar, LLP

(57) ABSTRACT

A pixel circuit acts as a sensing element in a sensing device. The pixel circuit includes a sensing electrode, a first gate electrically connected to the sensing electrode, a second gate in electrical communication with the first gate, and a readout device that is electrically connected to the second gate. An input voltage applied to the sensing electrode is amplified between the first gate and the second gate, the amplification being measured as an output signal from the readout device to perform a sensing operation. For example, the output signal may be relatable to pH, analyte measurements, or other properties of sample liquids analyzed by the sensing device. A sensing device may include multiple pixels disposed on a substrate, each pixel including said pixel circuit. Driver circuits controlled by control electronics are configured to generate signals that selectively address the pixels and to read out voltages at the sensing electrodes.

15 Claims, 13 Drawing Sheets

(56) References Cited

U.S. PATENT DOCUMENTS

| | | |
|---|---|---|
| 8,741,680 B2 | 6/2014 | Fife et al. |
| 8,940,569 B2 | 1/2015 | Bedell et al. |
| 10,460,143 B2 * | 10/2019 | Uehara ................ G06K 9/0002 |
| 2005/0230271 A1 | 10/2005 | Levon et al. |
| 2010/0137143 A1 * | 6/2010 | Rothberg ............. C12Q 1/6874 |
| | | 506/2 |
| 2010/0301398 A1 * | 12/2010 | Rothberg ............. G01N 27/414 |
| | | 257/253 |
| 2012/0176523 A1 | 7/2012 | Yoo et al. |
| 2013/0082936 A1 | 4/2013 | Islamkulov et al. |
| 2013/0200438 A1 | 8/2013 | Liu et al. |
| 2014/0106494 A1 | 4/2014 | Bedell et al. |
| 2015/0330941 A1 | 11/2015 | Smith et al. |
| 2016/0131613 A1 * | 5/2016 | Jayant ................. C12Q 1/6869 |
| | | 506/9 |
| 2016/0313282 A1 | 10/2016 | Shieh et al. |

OTHER PUBLICATIONS

Lee IK et al., "A self-amplified transistor immunosensor under dual gate operation: highly sensitive detection of hepatitis B surface antigen.", Nanoscale. Oct. 28, 2015;7(40):16789-97 (Abstract only).

Chin Y-L et al., "A novel pH sensitive ISFET with on chip temperature sensing using CMOS standard process", Sensors and Actuators B Chemical. vol. 76, 2001, pp. 582-593.

Guliga H. et al., "Extended gate field effect transistor (EGFET) integrated readout interfacing circuit for pH sensing", 2014 2nd International Conference on Electrical, Electronics and System Engineering (ICEESE), Dec. 9, 2014, pp. 11-14 (Abstract only).

Smith, J. et al., "Flexible ISFET Biosensor Using IGZO Metal Oxide TFTs and an ITO Sensing Layer", IEEE Sensors Journal. 14(4), Apr. 2014, pp. 937-938.

Go, J. et al., "Coupled Heterogeneous Nanowire—Nanoplate Planar Transistor Sensors for Giant (>10 V/pH) Nernst Response." ACS Nano, 6(7), 2012, pp. 5972-5979.

* cited by examiner

DC output potential VOUT of dual-gate ISTFT with feedback (VIN = constant V)

BIO-SENSOR PIXEL CIRCUIT WITH AMPLIFICATION

RELATED APPLICATION DATA

This application is a divisional application of U.S. application Ser. No. 15/204,359 filed on Jul. 7, 2016, the content of which is incorporated herein by reference.

TECHNICAL FIELD

The present invention finds application in active matrix sensor arrays of sensors using field effect transistors (FET) or thin-film transistors (TFTs). In particular, this invention relates to ion-sensitive thin-film transistor (ISTFT) sensor arrays.

BACKGROUND ART

Ion sensitive field effect transistors (ISFETs) are well known as pH sensitive biosensors, and are also capable of being used for biochemical sensing where the sensing gate surface is functionalized with a material for selective recognition of a target species. Arrays of ISFETs may be utilized for the multiplexed detection of multiple different species. Array-based measurement may also be used to measure a single quantity multiple times, thus minimizing errors in detection.

A known structure for ISFET sensing is the extended gate ISFET as described in Smith, J., Shah, S., Goryll, M., Stowell, J. and Allee, D., "Flexible ISFET Biosensor Using IGZO Metal Oxide TFTs and an ITO Sensing Layer", IEEE Sensors J. 14(4) pp. 937-938 (2014) (Smith et al.). According to the extended gate principle, the physical gate of the transistor is connected to a sensing electrode. The sensing electrode is a conductor (ITO) which is typically larger than the transistor gate. An extended gate sensor is described in "Smith et al". The drain-source and reference bias voltages are maintained constant and the current through the devices is measured as a function of time. This current is a function of the pH of a liquid in contact with the extended-gate ITO surface.

The use of dual-gated ISFETs for increased sensitivity is described in Go, J., Nair, P., Reddy, B., Dorvel, B., Bashir, R. and Alam, M., "Coupled Heterogeneous Nanowire-Nanoplate Planar Transistor Sensors for Giant (>10 V/pH) Nernst Response." *ACS Nano*, 6(7), pp. 5972-5979 (2012). A Si nanoplate-nanowire transistor pair is used as a dual-gate ISFET where changes in pH are determined by sweeping the gate voltage and measuring the IV response. Changes in potential at the nanoplate require larger shifts in potential at the nanowire in order to maintain the same current. In this way, the signal from the sensing of the nanoplate is amplified.

U.S. Pat. No. 8,415,716 (Rothberg et al., issued Apr. 9, 2013) describes improved array control and ISFET pixel designs facilitating increased measurement sensitivity and accuracy while allowing small pixel sizes and large arrays. Improvements are made upon the ISFET array designs of Milgrew et al. ISFET measurement linearity and dynamic range is sacrificed in order to relax the requirement for both n- and p-type transistors, reducing pixel complexity and size. Therefore, large dense arrays are possible, but measurement range is limited. Array control circuits are also disclosed including analogue-to-digital conversion on the same integrated circuit as the array but located outside of the sensor array region. In general, Rothberg et al. describes methods for signal processing in order to improve the signal to noise ratio rather than signal amplification, no in-pixel amplification of sensor signal.

US2005/0230271 (Levon et al., published Oct. 20, 2005) discloses an active matrix array of floating gate ISFETs. Sensing is performed by detection of the threshold voltage of two ISFETs, one of which is coated with a sensing material. The difference signal between the two ISFETs is amplified to give the output signal.

US2013/0200438 (Liu et al., published Aug. 8, 2013) describes the use of various dual-gate ISFETs for signal amplification in the detection of biomolecules at a sensing surface.

U.S. Pat. No. 8,247,849 (Fife et al., issued Aug. 21, 2012) describes a two transistor pixel circuit for forming an array of ISFETs.

U.S. Pat. No. 8,741,680 (Fife et al., issued Jun. 3, 2014) discloses further details for two transistor pixel circuits and explicitly describes active matrix implementation.

U.S. Pat. No. 8,940,569 (Bedell et al., issued Jan. 27, 2015) discloses a dual-gate ISFET operated in a constant current mode with amplification by means of an operational-amplifier based circuit. The possible use of such architecture as a pixel within an array is referred to, but no pixel circuit for such an implementation is shown.

SUMMARY OF INVENTION

A pixel circuit for an ion-sensitive sensor array circuit is comprised of a dual-gate ion-sensitive transistor, and a readout transistor. The pixel circuit is arranged so as to achieve amplification of an input voltage signal at a sensing electrode. The dual-gate ion-sensitive transistor has a first gate having a first capacitance to a channel of the device, and a second gate having a second capacitance where the first capacitance is larger than the second capacitance. The sensing electrode is connected to the first gate of the dual-gate ion-sensitive transistor, and the second gate of the ion-sensitive transistor is connected to a readout device. The top surface of the sensing electrode forms a sensing surface, or optionally the sensing surface may be coated by an insulating material to create a sensing surface.

By appropriately biasing the drain and source terminals of the dual-gate ion-sensitive transistor, for example by use of a current source, amplification of the input voltage signal is achieved between the first and the second stage of the ion-sensitive transistor. The amplified signal is measured by use of the readout transistor. Feedback is implemented between the input of the readout transistor and the drain of the dual-gate ion-sensitive transistor.

Arrangements whereby multiple pixel circuits may be configured to form a sensor array device are further described, comprising the addition of one or more additional transistors to perform row selection operations. Further embodiments describe how the amplification may be increased by incorporating additional amplification stages into the pixel.

Relatedly, a method of driving the pixel circuit is described whereby the ion-sensitive transistor is biased by a current source, and timing signals are applied to one or more row selection transistors to implement X-Y readout of an array of said pixel circuits comprising the sensor array device.

Advantages of the invention are as follows:

Amplification of the input signal with a dual-gate ion sensitive transistor enables increased sensitivity to changes in potential at the sensing electrode. This allows the measurement of smaller changes in pH or the detection of smaller numbers of biomolecules adsorbed on the sensing surface. Increased sensitivity improves the accuracy of measurements and expands the chemical and biochemical sensing applications possible with such sensor arrays.

Amplification of the signal within the pixel circuit prior to the readout transistor reduces the influence of noise arising from the rest of the array or from subsequent signal processing steps. Signal amplification outside of the pixel has the disadvantage of amplifying any noise inherent in the system. Signal amplification within the pixel itself is, therefore, a significant advantage of this invention. The increased signal to noise ratio (SNR) improves the precision of measurements as well as lowering the limit of detection of such sensors.

A small number of transistors are required for the pixel circuit, allowing pixels with small areas to be realized. Any reduction in the number, or size, of the components necessary to form a pixel circuit lowers the total area required for the pixel. This is particularly advantageous when forming large arrays of sensors as smaller pixel areas increase the density of such arrays, allowing a greater number of individual sensor elements within a given array area.

If the individual sensing surfaces of the sensors within these arrays are functionalized to specifically detect different targets, then a greater number of sensors will increase the level of multiplexed detection possible with the array.

Greater sensor numbers can also be used to increase the level of redundancy within the array. Multiple sensors can be used for error recognition during measurement and provide alternative sensors should there be a low yield of effective sensors resulting from the fabrication process.

The simple pixel design can be manufactured using a single channel process, reducing the number or processing steps and therefore the cost of producing large arrays.

According to certain described embodiments, an additional advantage is that very high factors of amplification can be achieved by cascading multiple amplification stages within the same pixel.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features.

DESCRIPTION OF REFERENCE NUMERALS

Figure 1:
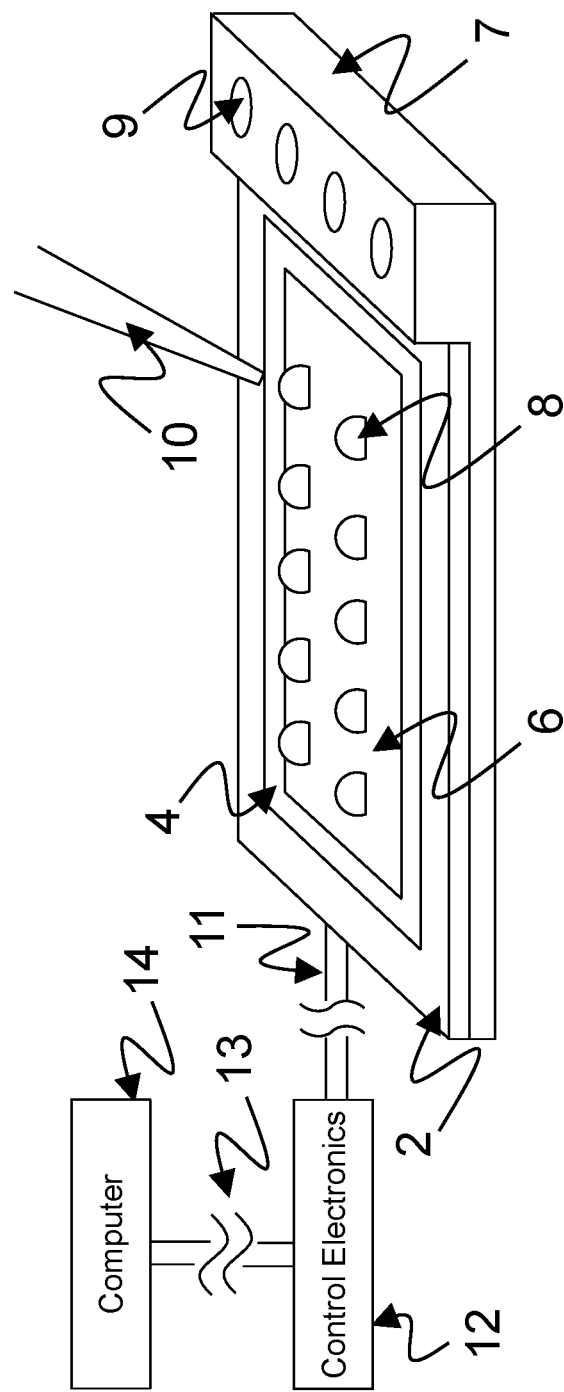
FIG. 1 is a schematic diagram depicting a microfluidic device with a sensor array comprised of thin-film electronics on a substrate and the associated control electronics.

2 Sensor array substrate
4 Thin film electronics
6 Sensor array
7 Microfluidic device
8 Liquid packets
9 Fluid inputs
10 Pipette
11 Connecting wires
12 Control electronics
13 Connecting wires
14 Computer
16 Pixel circuit
18 Column driver circuit
20 Row driver circuit
22 Serial interface
26 Voltage supply interface
28 Sensing surface
29 Sensing electrode
30 Passivation surface
32 Via connection
34 Insulating layer
36 Active region
37 Bottom gate of dual-gate ISFET
38 Bottom gate of dual-gate ISFET
39 Top gate of dual-gate ISFET
40 Top gate of dual-gate ISFET
41 Drain
42 Source
43 Insulating layer
44 Bottom gate insulator
46 Dual-gate ISTFT 47 Sensor element
48 Dual-gate ISTFT
49 Second stage amplification element
52 Capacitor
53 Transistor with extended gate
54 Transistor
56 Feedback connection between gate and drain
57 Second stage feedback connection
60 Readout transistor
62 Row select transistor
63 Row select transistor
64 Row select transistor
65 Row select transistor
68 Constant current source circuit
70 Transistor
72 Capacitor
74 Drive transistor
76 Transistor

DETAILED DESCRIPTION OF INVENTION

FIG. 1 is a schematic diagram depicting an exemplary ISTFT sensor array 6 configured for use as a pH or biochemical sensor. The array is configured to sense one or more properties (e.g. the pH) of one or more packets of liquid 8 present in the locations of one or more pixels on the array. The sensor array 6 may comprise a part of a microfluidic device 7, which may additionally and optionally comprise a means of introducing the liquid packets 8 to the sensor array 6 from fluid inputs 9, or from some sealed reagent storage, for example by means of channels, conduits, flows or any other such microfluidic means as is well known. Alternatively, an operator may introduce the liquid packets directly to the device, for example by means of a pipette 10. The liquid packets may comprise, for example, any one of; droplets, an emulsion or a gel. Alternatively, the array may be configured to sense a continuum of fluid covering a part or a whole of the physical extent of the array.

The liquid packets being sensed may typically be a polar material, may typically be an aqueous material, and may typically contain ions. The sensor array 6 may be controlled by means of thin film electronics 4, for example comprised of thin-film transistors (TFTs) supported on the surface of a sensor array substrate 2. The inputs and outputs to and from this sensor array are communicated via electrical connections, such as connecting wires 11 and 13, to control electronics 12 and a computer 14 or other electronic processing unit. Software is used to configure the control electronics to supply driving signals to the sensor array. The signal output from the array may be analogue and may be subsequently converted to a digital signal by means of the control electronics in a format for receiving, processing and displaying by the computer 14.

Figure 2:
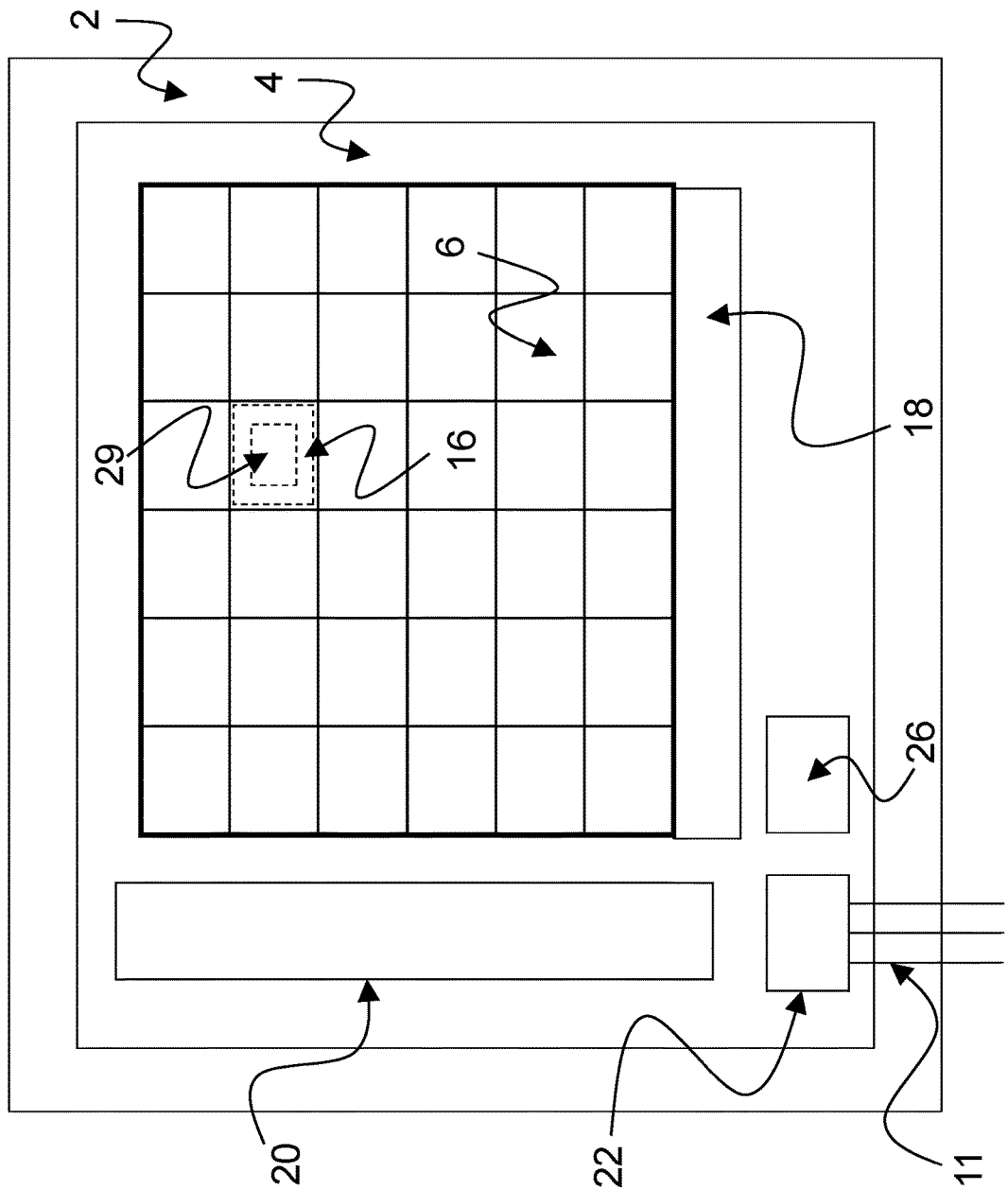
FIG. 2 is a schematic diagram depicting an exemplary arrangement of the thin-film electronics of the sensor array of FIG. 1.

FIG. 2 is a schematic diagram showing an exemplary arrangement of the sensor array 6 disposed upon the surface of the substrate 2 and driven by thin-film electronics 4. The top surface of the sensor array 6 comprises a plurality of sensing electrodes 29 configured within each pixel of the array; any element of which may be termed a pixel circuit 16.

Figure 3:
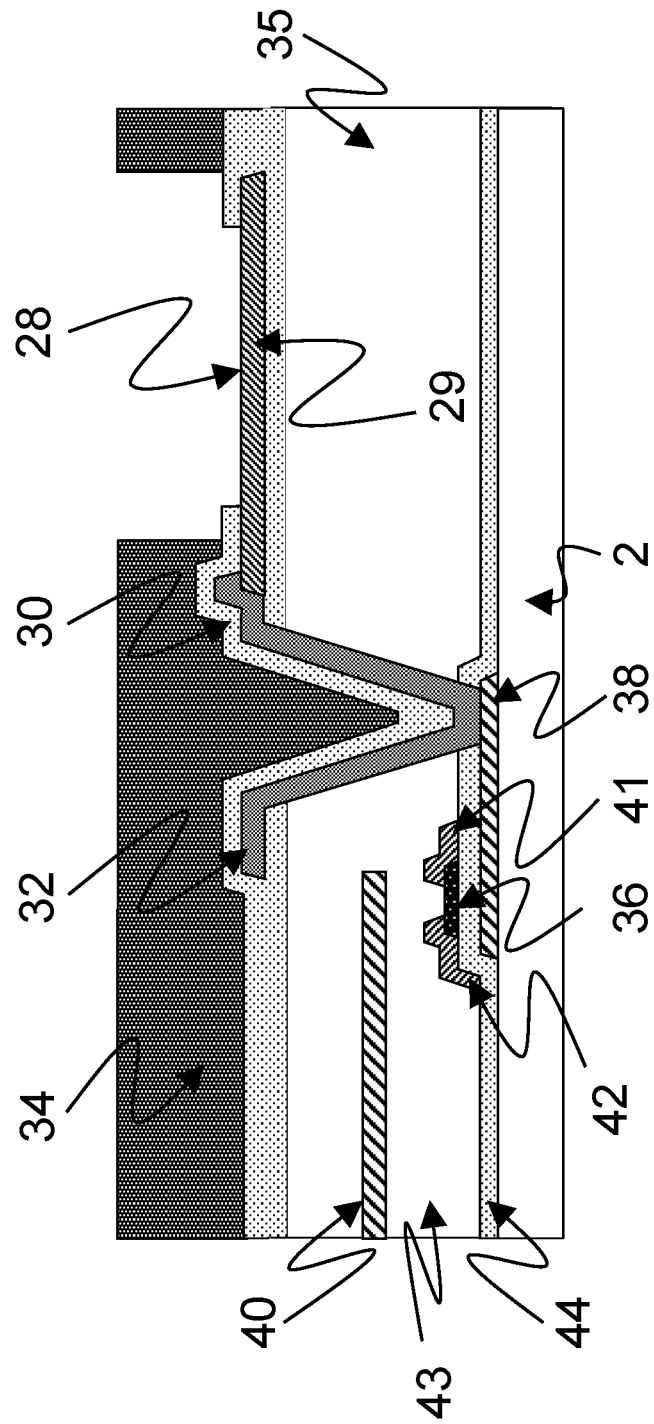
FIG. 3 shows a cross section through an exemplary dual-gate ISTFT that may be used as a sensor element within the pixels of the sensor array of FIG. 2.

A surface of the sensing electrode 29 is exposed to liquid and is termed the sensing surface 28 (see FIG. 3). Optionally the sensing electrode may be coated by an insulator to form the sensing surface.

The pixels 16 are addressed by means of thin-film electronics comprising row and column driver circuits, 20 and 18 respectively. A serial interface 22 and voltage supply interface 26 are connected to control electronics shown in FIG. 1 via connecting wires 11. Electrical signals may be generated by the row and column driver circuits for selectively addressing and reading out of an input signal (typically a voltage) present at the sensing electrode 29 of each individual pixel 16.

Generally, an aspect of the invention is a pixel circuit that acts as a sensing element in a sensing device. In exemplary embodiments, the pixel circuit is an extended-gate ISTFT device that includes a sensing electrode; a first gate electrically connected to the sensing electrode; a second gate in electrical communication with the first gate via an active region; and a readout device that is electrically connected to the second gate. An input voltage applied to the sensing electrode is amplified between the first gate and the second gate, the amplification being measured as an output signal from the readout device to perform a sensing operation.

FIG. 3 is a schematic diagram of a cross-section of an exemplary extended-gate ISTFT device. The ISTFT is supported by a substrate 2 and comprises an active region 36, drain 41, source 42, gate dielectric, or first or bottom gate insulator 44 and a bottom or first gate 38. The active region is in physical contact with or connected to an active region drain 41 at one side and with active region source 42 of the other side forming the channel of the transistor. The materials of the source, drain and active region may be comprised of suitable materials to form a transistor structure, typically semiconductor materials, e.g. silicon, gallium nitride or indium gallium zinc oxide (IGZO).

The bottom gate of the ISTFT 38 is connected by means of a via connection 32 through insulating layer 43 and passivation surface 30 to a sensing electrode 29. The sensing electrode 29 is typically comprised of a conductor or conductive material, for example aluminium or indium tin oxide (ITO). The upper surface of the sensing electrode 29 forms a sensing surface 28 which is exposed to liquid. Optionally, a layer of insulator material (not shown) may be disposed between the sensing electrode 29 and the sensing surface 28. Examples of insulator materials that may be used include silicon dioxide, aluminium dioxide and tantalum dioxide. Alternatively, the insulating layer may be comprised of a semiconducting material for example silicon.

The bottom gate 38 and sensing electrode 29 physically form a structure that is termed the extended gate. The physical area of the sensing electrode 29 is typically larger than that of the bottom gate 38, for example by a factor of 2, by a factor of 10, by a factor of 100 or by a factor of 1000. The large area of the sensor electrode 29 (and correspondingly of the sensing surface 28) may facilitate a greater sensitivity to the properties of the liquid than would be the case if the area of the sensing electrode 29 and bottom gate were the same.

The physical material forming the sensing surface may be chosen according to the desired mode of sensing of the device. For example, the device may be configured to be sensitive to the pH of the liquid if the surface contains OH— groups (as, for example, in the case where the surface is comprised of silicon dioxide, or of aluminium dioxide, or of ITO). As an alternative example, the surface may be configured to be sensitive to certain chemical or bio-chemical species, e.g. DNA, proteins, antibodies. Biochemical coatings may be added to the surface, e.g. antibodies, aptamers, proteins to aid in bio-chemical detection or to make the sensitive specific to a desired target species (e.g. a specific protein).

Optionally, and preferably, an insulating layer 34 may be used to passivate the surface exposed to liquid away from the sensing surface 29, for example to prevent any conductive paths forming between the liquid and the source, drain or channel of the ISTFT.

Optionally, the insulating layer 34 may comprise the same material, or may be formed in the same process as any insulator disposed between the sensing electrode 29 and the sensing surface 28.

Also shown in FIG. 3 is a second gate 40, or top gate, located above the active region of the TFT. In this regard, the terms "top" and "bottom" are convenient references in relation to the specific depictions in the figures, but is not meant to limit the device configuration to any particular orientation. Accordingly, the bottom and top gates more generally may be referred to respectively as first gate 38 and second gate 40. The bottom gate 38 and top gate 40 both have electrical communication with the active region, where the bottom gate is insulated from the active region by a bottom gate insulator 44 and the top gate is insulated from the active region by a top gate insulator 43. This structure thus comprises a dual-gate TFT. The conductivity of the active region is modified in accordance with the potentials applied to the source, drain, top gate electrode and bottom gate electrodes of the TFT structure.

An approximate effective gate potential VG of this dual-gate TFT is described by equation 1:

$$VG = \frac{\alpha VBG + VTG}{1 + \alpha}, \quad \text{(Equation 1)}$$

where the electrical potential of the top gate electrode 40 is denoted VTG and the electrical potential on the bottom gate electrode 38, is denoted VBG. The ratio of the capacitance between the active region 36 and the bottom gate electrode, i.e., a first gate capacitance, and the capacitance between the active region and the top gate electrode, i.e., a second gate capacitance, is included as the term α. The value of α may be controlled by means of the ratios of the thicknesses of the insulating regions 44 and 43 or their relative electrical permittivity.

The current between the drain and source terminals of the TFT may in effect be uniquely defined by the voltage at the drain and at the source and by the value of VG. The current between the drain and source terminals will in general have a typical thin-film transistor characteristic as is well known.

For the purposes of explanation, we now consider the case where a constant current is sourced between the drain and source of the TFT, and the drain and source voltages are also maintained constant. In this situation, if the drain-source current is to remain constant, any change in the bottom gate potential must be compensated for by a change in the potential on the top gate, such that VG remains constant in accordance with Equation 1. The condition of equation 2 therefore applies describing the relationship between any perturbation between the potentials VTG and VBG:

$$\Delta VTG = -\alpha \times \Delta VBG \quad \text{(Equation 2)}$$

In this regard the dual-gate TFT may be configured as a voltage amplifier between the top and bottom gate structures, in the case where the drain and source terminals are suitably biased.

Figure 4:
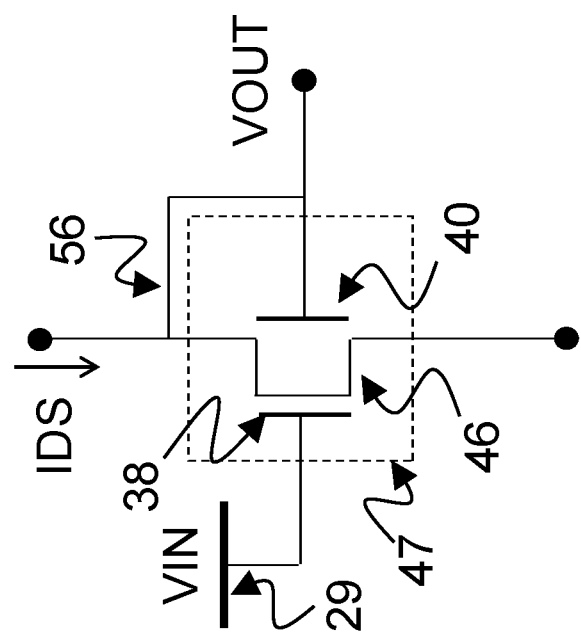
FIG. 4 is a schematic diagram depicting a dual-gate ISTFT sensor element with feedback according to a first embodiment of the invention.

FIG. 4 is a circuit representation of a dual-gate ISTFT 46 of FIG. 3 configured as a sensor element 47. Such a sensor element may be used within a pixel 16 of the sensor array of FIG. 2. The dual-gate transistor has terminals at the drain, source, bottom gate 38 and top gate 40, with the bottom gate connected to sensing electrode 29 of FIG. 3. The top gate is electrically connected to the drain, shown by the connecting wire 56 which provides a feedback connection between the top gate and the drain of the dual-gate transistor 46. Feedback may be achieved, for example, by forming a suitable via between the appropriate layers of the physical device structure. The potential at the sensing electrode 29 is depicted as VIN, and the potential at the top gate 40 as VOUT. The circuit is also depicted as having a drain-source bias such that a current IDS flows through the transistor.

In a constant current mode of operation, any small perturbation of the potential VIN at the sensing electrode 29, and therefore of the potential at the bottom gate 38, may be amplified with an appropriate choice of gate capacitance ratio α. However, with the inclusion of feedback the change in potential at the top gate 40 does not follow the simple relationship shown in Equation 2. The simulated performance of this dual-gate TFT with feedback is discussed in the following sections.

Figure 5:
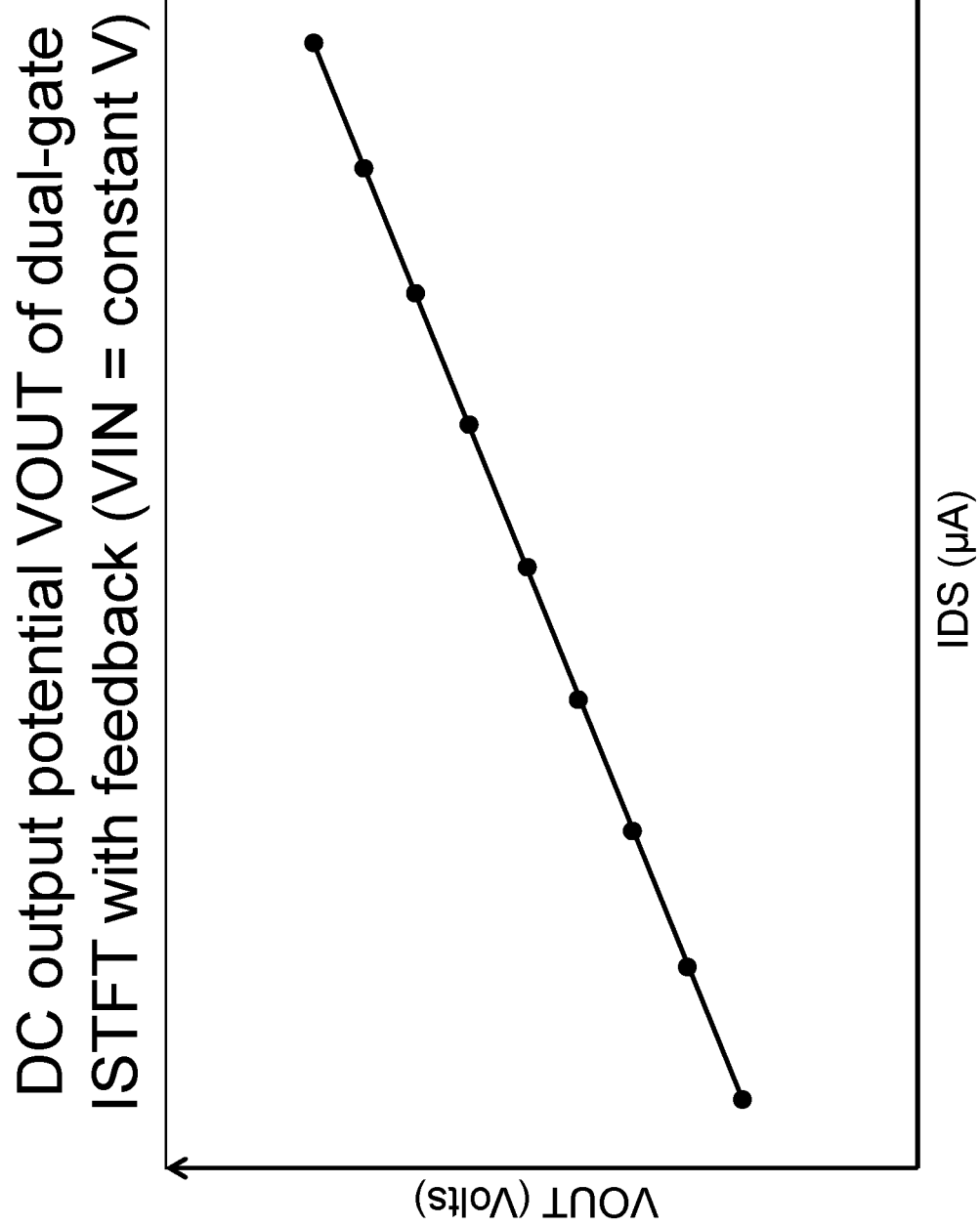
FIG. 5 is a plot of the simulated DC output of a dual-gate ISTFT sensor element with feedback of FIG. 4 according to a first embodiment of the invention.

FIG. 5 is a plot of the simulated DC output of the dual-gate TFT with the feedback circuit of FIG. 4. The vertical axis of the graph shows the DC potential VOUT at the top gate 40 of the TFT, and the horizontal axis is the drain-source current IDS through the same TFT. In the simulation, the potential VIN at the bottom gate 38 is held constant as is the potential at the source of the TFT. The drain-source current through the TFT is changed by varying the DC bias at the drain of the TFT. However, as the drain is connected via feedback 56 to the top gate 40, the potential at the drain is also the potential at VOUT. The linear relationship between the DC potential at VOUT and the current IDS is shown in FIG. 5. The exact values of this plot will depend upon the ratio between the gate capacitances, a, of the bottom (or first gate) capacitance to the top (or second) gate capacitance of the dual-gate TFT, which may be of the value 2, 5, 10 or 20.

Figure 6:
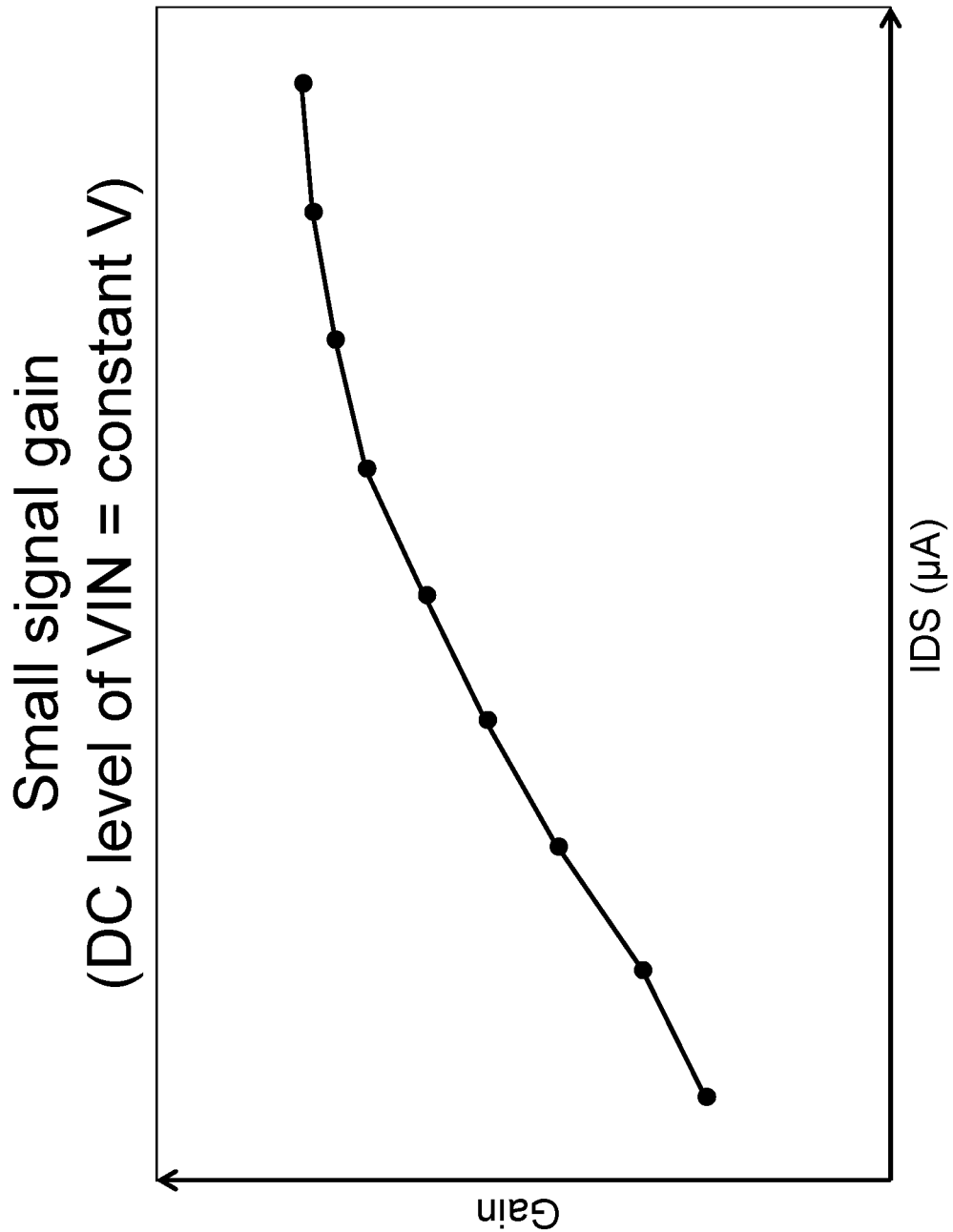
FIG. 6 is a plot of the simulated small signal gain of a dual-gate ISTFT sensor element with feedback of FIG. 4 according to a first embodiment of the invention.

FIG. 6 is a plot of the simulated small signal gain of the dual-gate TFT with feedback circuit of FIG. 4. The vertical axis shows the small signal gain between VIN and VOUT of FIG. 4. The horizontal axis shows the drain-source current IDS through the TFT. In the simulation, the DC level of the gate-source potential VIN of the bottom gate is held constant as in FIG. 5. However, a small AC signal is also applied to the bottom gate. When the dual-gate TFT is operated in a constant current mode, any small perturbation at the bottom gate is amplified at the top gate. Therefore, there is signal gain between the bottom and top gates and correspondingly between VIN and VOUT. The dependence of the small signal gain upon the current IDS through the TFT is shown in the plot of FIG. 6. A constant current IDS may be supplied by connection to an external constant current source. When operated at higher values of IDS the small signal gain of the circuit increases, which tends to a limit at high currents. With the choice of an appropriate drain-source current at which to operate the TFT, the small signal gain of the circuit can be maximised. The current IDS supplied by the constant current source. The term "constant current" is intended to mean constant within known or suitable tolerances as may occur, i.e., the current may be held constant to within an accuracy determined to be sufficient for successful operation of the device, varying by, for example, 1, 2, 5 or 10% depending upon the particular device.

Figure 7:
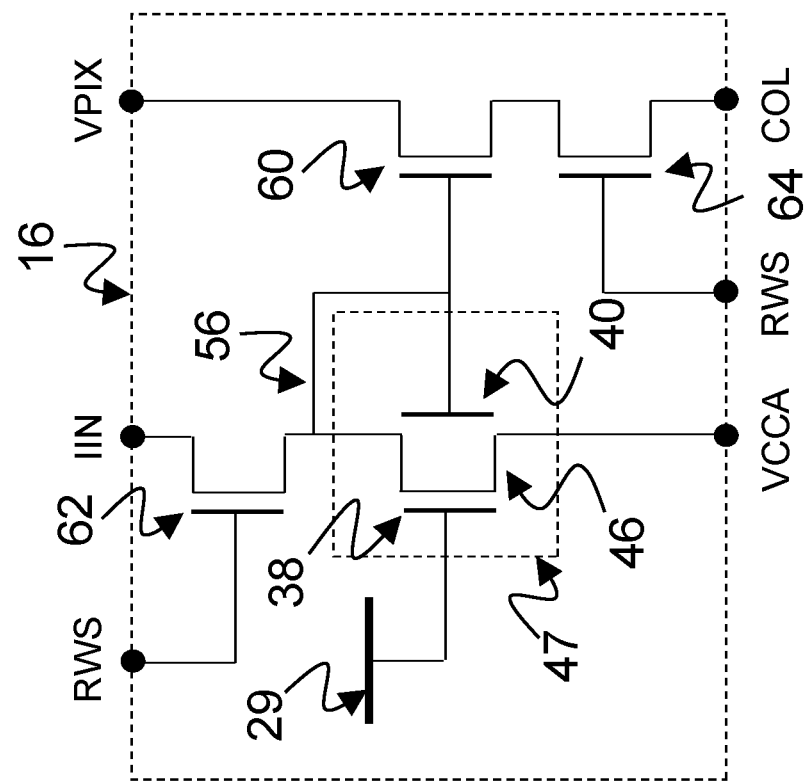
FIG. 7 is a schematic diagram depicting a pixel circuit for use in the sensor array of FIG. 2 according to a first embodiment of the invention.

FIG. 7 is a schematic diagram showing a circuit representation of a pixel 16 of the sensor array of FIG. 2 according to a first embodiment of the invention. The pixel circuit 16 comprises a dual-gate sensing TFT 46 configured as the sensing element 47 of the pixel. The first gate (or bottom gate) 38 is connected to the sensing electrode 29 and feedback between the second gate (or top gate) and drain of the TFT is achieved with the connection 56. In these respects the circuit presented in FIG. 7 is similar to that depicted in FIG. 4. The pixel circuit of FIG. 7 further includes row select elements configured to receive timing signals for addressing the pixel circuit. The row select elements may include a row select transistor located between the current supply input and the feedback connection between the second gate and the drain terminal of the dual-gate TFT configured as a sensing element. The row select elements may also include a row select transistor located between the current sink connection and the source terminal of a readout transistor configured as a readout device. Referring to FIG. 7, this circuit is made suitable for use as a pixel circuit within an array such as that depicted in FIG. 2 by the addition of a readout transistor 60 and row select transistors 62 and 64.

Driving signals are applied to the terminals of the pixel circuit as follows:

DC bias applied to VCCA
DC bias applied to VPIX
Timing pulse applied to RWS
Current sink at COL A description of the operation of the pixel circuit 16 is as follows:

The dual-gate ISTFT 46 serves as the sensing element 47 within this configuration of the pixel circuit 16. This dual-gate ISTFT is operated in a constant current mode as described in relation to FIG. 4 by connection to a constant current source through the column line IIN and with the application of a DC bias at the ISTFT source with signal VCCA. The signal at the sensing electrode 29 is amplified by this dual-gate ISTFT through to the gate of the readout transistor 60.

The supply of current to the ISTFT of an individual pixel within an array is controlled by means of a timing signal RWS applied to transistor 62. This transistor only allows current to flow through the ISTFT when both RWS and IIN are high. In this way an array of ISTFT can be addressed with current flowing only through the pixel being sensed.

The readout device may be configured as a readout transistor 60 that is configured as a source follower, such that the amplified signal from the dual-gate TFT may be read out from the pixel through the output line COL. This transistor is externally biased by VPIX and a current sink at COL. Current flow through readout transistor 60 is controlled by means of a timing signal RWS applied to the gate of transistor 64. When RWS is high the signal from the pixel may be read at COL. In this way the signal from each pixel within an array may be read sequentially.

Advantages of the invention area as follows:

Amplification of the input signal with a dual-gate ion sensitive transistor enables increased sensitivity to changes in potential at the sensing electrode. This allows the measurement of smaller changes in pH or the detection of smaller numbers of biomolecules adsorbed on the sensing surface. Increased sensitivity improves the accuracy of measurements and expands the chemical and biochemical sensing applications possible with such sensor arrays.

Amplification of the signal within the pixel circuit prior to the readout transistor reduces the influence of noise arising from the rest of the array or from subsequent signal processing steps. Signal amplification outside of the pixel has the disadvantage of amplifying any noise inherent in the system, potentially obscuring the measurement from the ISTFTs on the array. Signal amplification within the pixel itself is, therefore, a significant advantage of this invention. An increased signal to noise ratio (SNR) will improve the precision of measurements possible with ISTFTs in arrays as well as lowering the limit of detection of such sensors.

A small number of transistors are required for the pixel circuit. This design is therefore simpler than other designs, such as U.S. Pat. No. 8,940,569, which typically require larger components or more transistors within the array element circuit and may also typically have a greater number of row or column addressing lines. Reducing the complexity and the number of transistors in the array element circuit 16 is advantageous as it allows smaller array elements. Typically, it is often the case that the minimum achievable array element size is set by the limitations of the thin-film electronics and the design for fabrication requirements (design rules) dictating the layout of the array element circuit 16 in thin-film electronics. A simpler circuit (fewer transistors) therefore enables smaller array elements to be designed and fabricated, allowing pixels with small areas to be realized. This is particularly advantageous when forming large arrays of sensors as smaller pixel areas increase the density of such arrays, allowing a greater number of individual sensor elements within a given array area.

Greater numbers of sensor elements within an array allow more samples to be simultaneously assayed during measurement. If the individual sensing surfaces of the sensors within these arrays are functionalized to specifically detect different targets, then a greater number of sensors will increase the level of multiplexed detection possible with the array.

Greater sensor numbers can also be used to increase the level of redundancy within the array. Multiple sensors can be used for error recognition during measurement and provide a greater number of alternative sensors for measurement should some pixels be defective.

An additional advantage of the smaller and simpler design of array element circuit 16 is the possibility of increased manufacturing yield and hence lower cost of the device.

This invention can be implemented with only n-type transistors. It is therefore possible for an ISTFT array to be fabricated in a single channel process (n-type only), whereas components such as op-amps have a much lower performance in a single channel process. Compared to a complementary process (which has both n- and p-type transistors), a single channel process may be considerably lower cost since fewer process steps are required for fabrication. With a single channel process it also becomes possible to fabricate the sensor array in manufacturing processes that only support single channel transistors, e.g. standard display processes for the fabrication of amorphous silicon (a-Si), zinc oxide (ZnO) or Indium Gallium Zinc Oxide (IGZO) processes.

Figure 8:
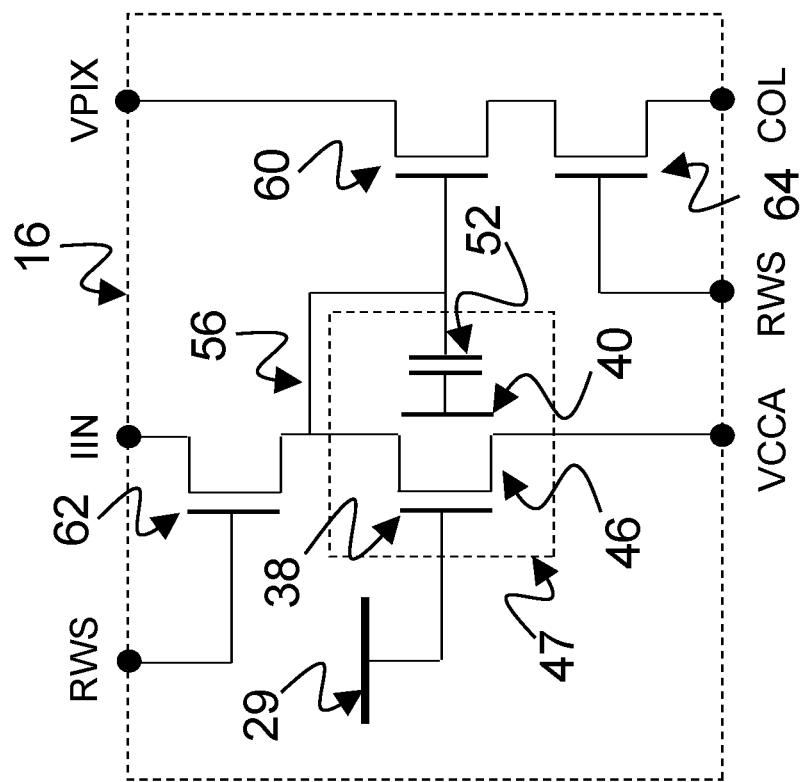
FIG. 8 is a schematic diagram depicting a pixel circuit for use in the sensor array of FIG. 2 according to a second embodiment of the invention.

A pixel circuit according to a second embodiment of the invention is as the first with an alternative configuration of the sensor element 47 as shown in FIG. 8. In addition to the dual-gate ISTFT, the sensor element contains a capacitor 52 located between the second gate 40 of the TFT and the node leading to the feedback connection 56 and the gate of the readout transistor 60.

The gain of a dual-gated ISFET can be altered by choosing a different ratio of the gate capacitances $\alpha$, as shown in equation 2. The dual-gate ISTFT shown in FIG. 8 is a circuit representation of an ISTFT of the type depicted in FIG. 3, where the first gate 38 and second gate 40 are shown. The value of α may be controlled by means of the ratios of the thicknesses of the insulating regions 43 and 44 disposed between these gates and the TFT active region shown in FIG. 3. Alternatively, a change in the relative electrical permittivity of regions 43 and 44 will also change the value of α.

Inclusion of a capacitor 52 located between the second gate of the dual-gate ISTFT and the feedback connection 56 provides additional gain within the sensing element 47 without altering the design or physical properties of the dual-gate ISTFT. When the capacitance of 52 is small compared to the capacitance at the second gate 40, and the circuit operation is as the first embodiment in a constant current mode, there will be amplification of the signal at the sensing electrode 29 through to the readout transistor 60. This amplification will be higher with the capacitor 52 connected to the ISTFT than would be the case with the same ISTFT alone.

This is advantageous as it allows different, and higher, choices of signal gain with the same design of dual-gate ISTFT. This allows higher values of gain within the pixel circuit without large increases in the complexity of the design, reducing the overall cost of the array.

Figure 9:
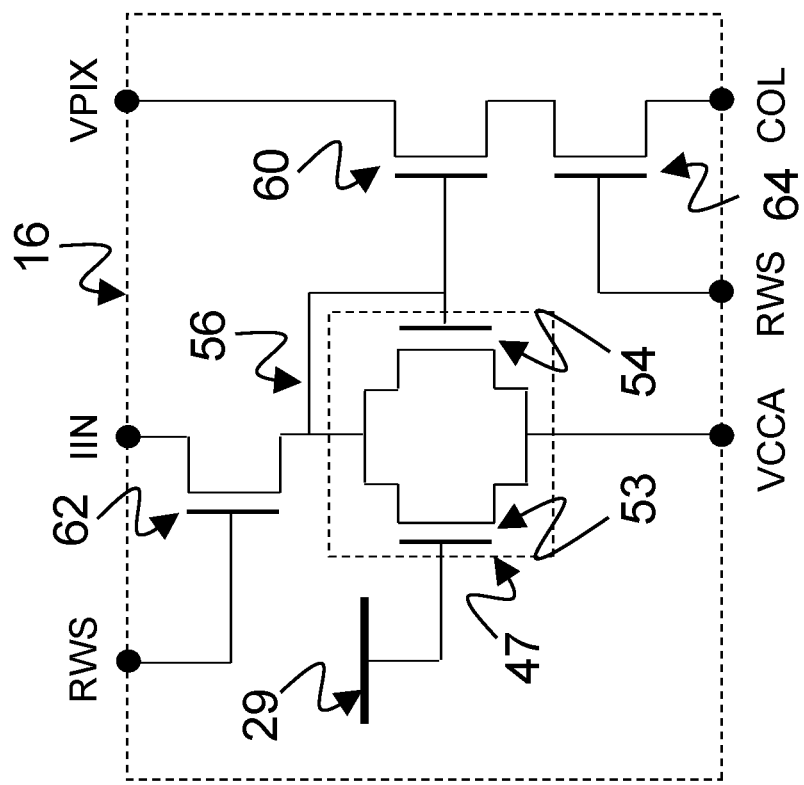
FIG. 9 is a schematic diagram depicting a pixel circuit for use in the sensor array of FIG. 2 according to a third embodiment of the invention.

A pixel circuit according to a third embodiment of the invention is as the first with an alternative configuration of the sensor element 47 as shown in FIG. 9. Instead of a dual-gate ISTFT, two transistors, 53 and 54, are connected in parallel. The gate of one of transistors 53 is an extended gate connected to the sensing electrode 29, with the gate of the other transistor 54 connected to the node leading to the feedback connection 56 and the gate of the readout transistor 60. Transistor 53 has a larger width than transistor 54. Typically the ratio of the width of transistor 53 to the width of transistor 54 may be quite large, for example 2 or 5 or 10 or 20.

The operation of the pixel circuit of the third embodiment is as follows. A constant current flows through the series combination of transistors 53 and 54, apportioned between the two transistors in a manner that depends on the potentials at each of their gates. If the potential at the gate of transistor 53 (connected to the sensing electrode) increases, in order for the current to remain constant, the potential at the gate of transistor 54 must decrease. As a consequence of the difference in widths of transistors 53 and 54, a relatively small change in the potential at the gate of transistor 53 (the sensing electrode) is accompanied by a larger change in the potential at the gate of transistor 54, thereby achieving amplification. Consequently, the arrangement operates in a similar way to that described in previous embodiments, the amplification being controlled by the different widths of the two transistors.

An advantage of this embodiment is that amplification may be achieved without recourse to a dual gate TFT. This embodiment may be especially suitable, for example, for implementation in processes where a dual gate TFT cannot be realised (or easily realised), for example a standard Low Temperature PolySilicon (LTPS) process.

This configuration of the sensing element 47 may require a larger total physical area in layout for two transistors compared to the single dual-gate ISTFT in the first embodiment. However, reducing the complexity of the manufacturing process may also reduce the overall cost of the array.

Figure 10:
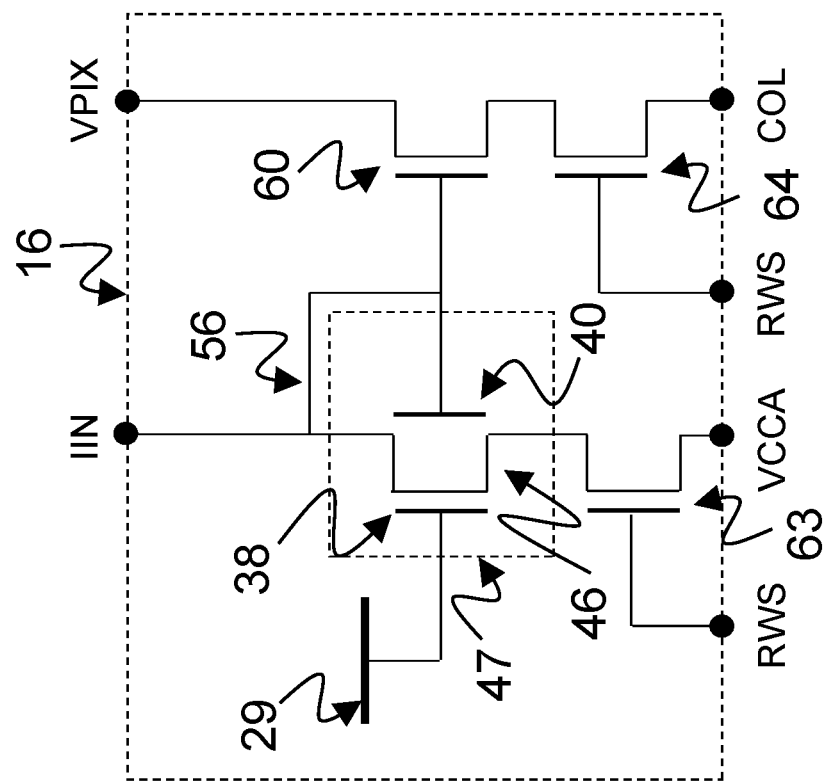
FIG. 10 is a schematic diagram depicting a pixel circuit for use in the sensor array of FIG. 2 according to a fourth embodiment of the invention.

A pixel circuit according to a fourth embodiment of the invention is as the first with an alternative placement of a row selection transistor 63 as shown in FIG. 10. The row select elements may include a row select transistor located between the sensing element and an input bias connection to the source terminal of the sensing element. In the first embodiment the row selection transistor 62 is located between the current supply column IIN and the feedback connection 56 at the drain of the dual-gate ISTFT. In this fourth embodiment a row selection transistor 63 is located between the source terminal of the dual-gate TFT configured as sensing element 46 and the VCCA bias connection. The sensing element 47 in this fourth embodiment may be configured according to the first, second or third embodiments.

This row selection transistor 63 allows current to flow through the sensing element 47 only when both the RWS signal applied to the gate of transistor 63 and IIN are high. In this way current may be supplied to only that pixel being sensed within an array.

An advantage of the fourth embodiment is that the gate to source voltage of the row select transistor 63 is increased when this transistor is turned on. This will decrease any voltage drop across this transistor when turned on, therefore improving the performance of the circuit.

Figure 11:
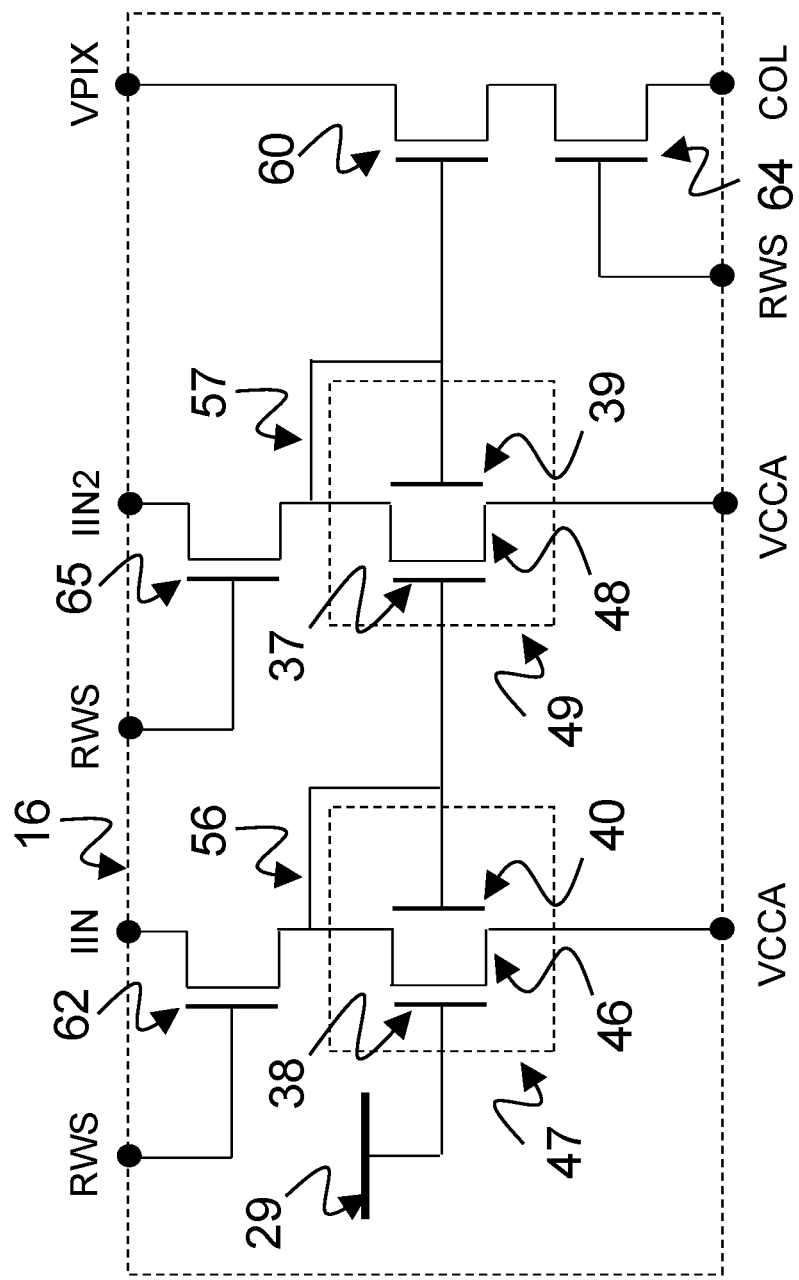
FIG. 11 is a schematic diagram depicting a pixel circuit for use in the sensor array of FIG. 2 according to a fifth embodiment of the invention.

A pixel circuit according to a fifth embodiment of the invention is as the first with an additional amplification stage of the signal, shown in FIG. 11. Generally, the first gate and the second gate comprise a first amplification element, and the pixel circuit further comprises a second amplification element connected between an output of the first amplification element and the readout device. The second amplification element comprises a third gate electrically connected to the output of the first amplification element, and a fourth gate in electrical communication with the third gate, wherein the fourth gate is electrically connected to the readout device.

Referring to FIG. 11, the sensing element 47 of this embodiment may be configured according to the first, second or third embodiment. A second amplification stage in this pixel circuit is located between the sensing element 47 and readout transistor 60. This secondary stage includes an amplification element 49, row selection transistor 65, feedback connection 57 and additional connections to timing signal RWS and potential bias VCCA, with an independent connection to another constant current source though column line IIN2. The secondary amplification stage element 49 may be the same circuit as the sensing element 47 in this pixel circuit, or it may be different from the sensing element according to the configurations of the sensing element 47 in the first, second and third embodiments of the invention.

The second amplification element 49 is located such that the output from the sensing element 47 is connected to the input of the amplification element 49. In FIG. 11 this is shown as a connection between the second gate 40 of the dual-gate TFT 46, configured as the sensing element 47, and the third gate 37 of the dual-gate TFT 48, configured as the amplification element 49. The output from this second stage is connected to the readout transistor 60, shown in FIG. 11 as a connection between the fourth gate 39 of the dual-gate TFT 48 and the gate of the readout transistor 60.

A feedback connection 57 is depicted between the second gate 39 and drain of the amplification element 49 configured as a dual-gate TFT 48. A further row selection transistor 65 is located between the second constant current source input IIN2, with the timing signal RWS connected to the gate of this transistor 65. The source of the dual-gate ISTFT 48 is connected to the potential bias VCCA.

Amplification with this second stage is achieved in the same manner as that described for the sensing element 47 in the first embodiment. The function of the element 49 is to provide gain which, in the configuration shown, is amplification of the signal between the third gate 37 and fourth gate 39. With the inclusion of the feedback connection 57, the small signal gain of this second stage is the same as that described for the circuit shown in FIG. 4 and within FIG. 7.

The dual-gate TFT 48 constituting the amplification element 49 is supplied with the constant current required to operate through column line IIN2. The source of the dual-gate TFT 48 may be biased with the same DC bias potential VCCA as the source of the first stage dual-gate ISTFT. However, each stage has its own independent constant current source through independent connections IIN and IIN2.

Supply of current though the second stage is controlled by means of a row selection transistor 65 which receives a timing signal RWS at its gate. The full pixel circuit operates only when RWS, IIN and IIN2 are high. In this way current to both amplification stages within the pixel circuit is supplied only to the pixel which is being sensed. The output from this second stage of amplification from element 49 is read at the gate of readout transistor 60 according to the first embodiment shown in FIG. 7.

A cascade of multiple stages of amplification of this type could be used to achieve very high signal gains. The complexity of the design can be limited by the repeated use of the same circuit configuration for the sensing element 47 and multiple amplification elements 49. In this way the cost of an array of such pixel may be reduced.

The utility of this multi-stage amplification depends upon the relative influence of the noise from the amplification stages within the pixel and the post-processing of the signal outside the pixel. If the noise due to the signal processing is small, then this high signal gain within the pixel circuit will be of limited value in improving the SNR if it also introduces high levels of noise. However, if the influence of the noise from the signal processing electronics outside of the pixel is large, then increased amplification within the pixel will reduce the influence of this noise upon the overall signal, improving the SNR.

Using any of the above structures, an aspect of the invention is a method of driving a pixel array sensing device comprising a plurality of pixels. Each pixel in the pixel array acts as a sensing element in the sensing device, and each pixel includes a pixel circuit in accordance with any of the described embodiments, including for example a sensing electrode; a first gate electrically connected to the sensing electrode; a second gate in electrical communication with the first gate via an active region; and a readout device that is electrically connected to the second gate. The driving method comprising the steps of biasing each pixel circuit with a constant input current source; applying timing signals to one or more row selection elements to selectively address one or more of the pixel circuits; perturbing an input voltage to the sensor element in each of the addressed pixel circuits, wherein the input voltage applied to the sensing electrode is amplified between the first gate and the second gate in each of the addressed pixel circuits; and reading out an output signal from the readout device in each of the addressed pixel circuits to perform a sensing operation. As an alternative to perturbing the input voltage, the input current source may be perturbed for performing the sensing operation.

Figure 12:
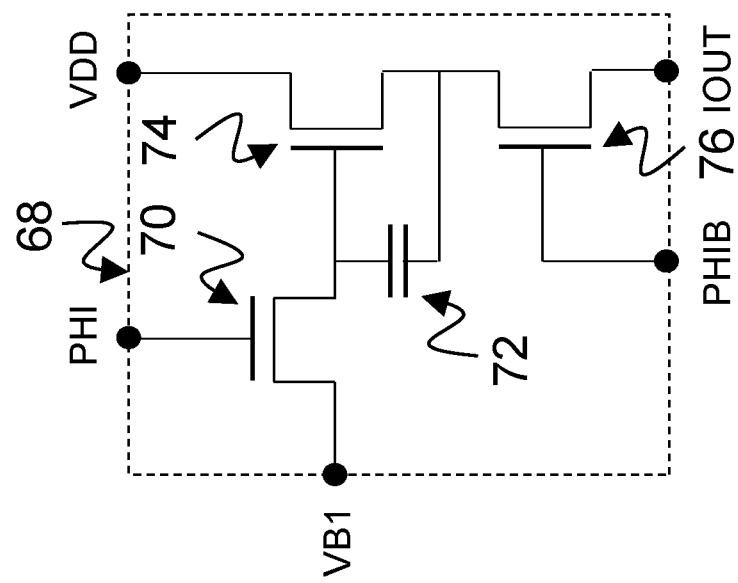
FIG. 12 is a schematic diagram depicting an exemplary constant current source circuit for use in suppling IIN to a pixel circuit of FIG. 7 according to a first embodiment of the invention.

FIG. 12 is a circuit diagram of an exemplary constant current source circuit 68 that may be used to supply IIN to a pixel circuit of FIG. 7 in accordance with a first embodiment of the invention. This same current source circuit may also be used to supply IIN to pixel circuits of FIGS. 8, 9 and 10 in accordance with second, third and fourth embodiments of the invention respectively. Two independent current sources of the same circuit configuration may also be used to supply IIN and IIN2 separately to a pixel circuit of FIG. 11 in accordance with a fifth embodiment of the invention. Constant current sources compatible with complementary process, including both n- and p-type transistor, are well known. However, constant current sources for single channel processes with only n-type are more difficult to achieve. The circuit shown in FIG. 12 is an example of a constant current source that is compatible with a signal channel process.

The circuit comprises a drive transistor 74, the drain of which is connected to DC bias potential VDD. A storage capacitor 72 is connected in parallel between the gate and source of the drive transistor 74. The gate of the drive transistor 74 is connected to a reference voltage VB1. This connection is switched by means of a transistor 70, the gate of which is connected to a clock signal PHI. The source of the drive transistor 74 is connected to an output IOUT. This connection is switched by means of a transistor 76, the gate of which is connected to a clock signal PHIB.

Figure 13:
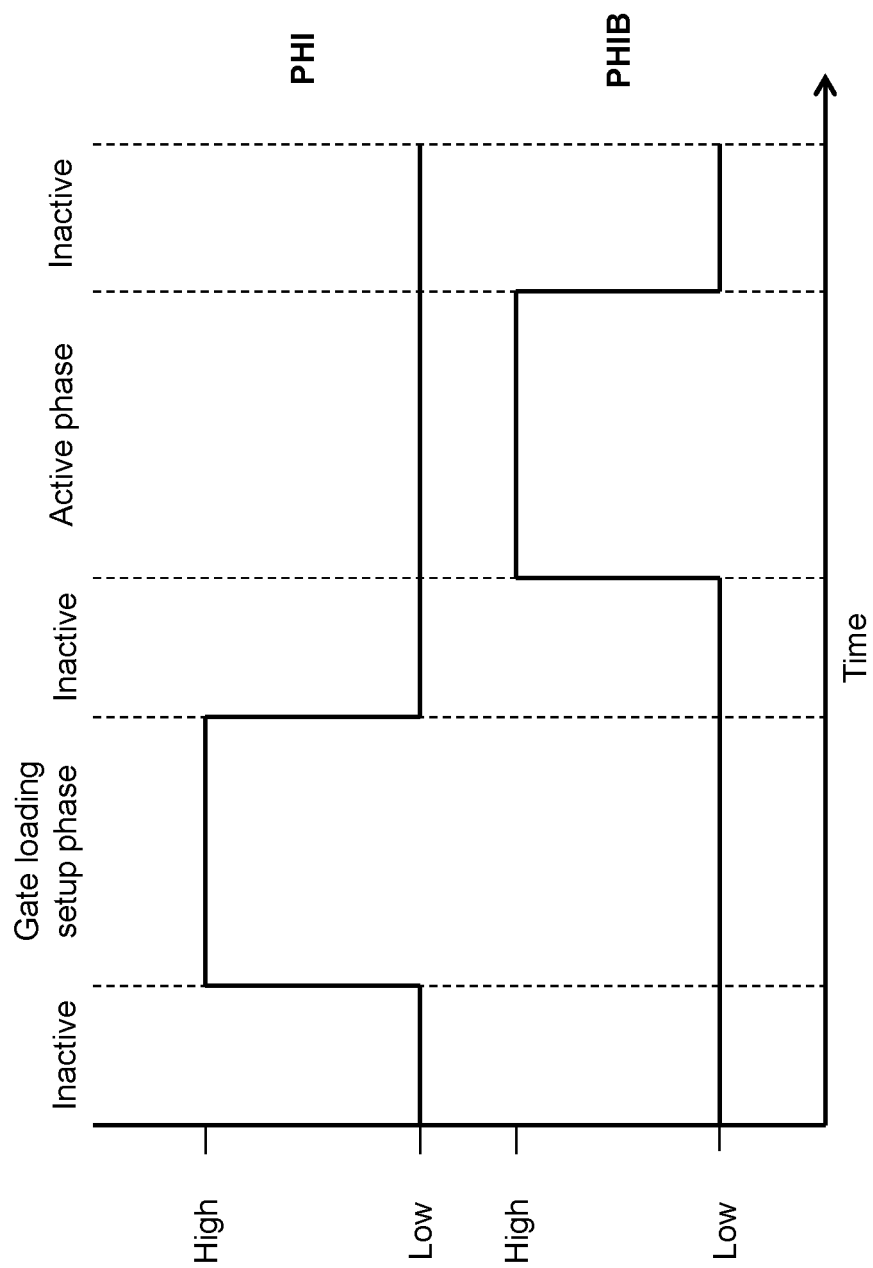
FIG. 13 is a timing diagram showing timing signals for the constant current source circuit of FIG. 12.

The current source operates in two phases, controlled by non-overlapping clocks PHI and PHIB, the timing signals for which are depicted in FIG. 13. The first stage involves the activation of PHI as a set-up phase. A reference voltage VB1 is programmed to the gate of the drive transistor 74 and stored on the capacitor 72. In the second stage, PHIB is taken high for an activated phase. With VDD set as a constant the loading of the circuit at IOUT results in the potential of the source and gate of the drive transistor changing together. The current source is non-ideal to the extent that the current is independent of the drain-source voltage of drive transistor 74. For this reason the drive transistors are made long. In this way a constant current may be supplied to IIN of a pixel circuit 16 for the constant current operation of the sensing element 47.

An aspect of the invention, therefore, is a pixel circuit that acts as a sensing element in a sensing device. In exemplary embodiments, the pixel circuit may include a sensing electrode, a first gate electrically connected to the sensing electrode, a second gate in electrical communication with the first gate via an active region, and a readout device that is electrically connected to the second gate. An input voltage applied to the sensing electrode is amplified between the first gate and the second gate, the amplification being measured as an output signal from the readout device to perform a sensing operation. The pixel circuit further may include one or more of the following features, either individually or in combination.

In an exemplary embodiment of the pixel circuit, the active region is connected to an active region drain and an active region source to form a transistor comprising a channel between the first gate and the second gate.

In an exemplary embodiment of the pixel circuit, the first gate is connected to the sensing electrode by a via connection through an insulating layer and a passivation surface.

In an exemplary embodiment of the pixel circuit, a physical area of the sensing electrode is larger than a physical area of the first gate by at least a factor of two.

In an exemplary embodiment of the pixel circuit, the first gate is associated with a first gate capacitance and the second gate is associated with second gate capacitance, and the first gate capacitance is larger than the second gate capacitance. A drain connected to the first gate is configured to receive a constant input bias current, and amplification of the input voltage is based on a capacitance ratio of the first gate capacitance to the second gate capacitance.

In an exemplary embodiment of the pixel circuit, the pixel circuit further includes a current source circuit configured to supply the constant input bias current, wherein the current source circuit is configured to receive timing signals for controlling a timing of the constant input bias current.

In an exemplary embodiment of the pixel circuit, the first gate and the second gate are in electrical communication with the active region via a first gate insulating layer and an insulating region between the first gate and the second gate, and the first and second gate capacitances are based on thicknesses of the first gate insulating layer and the insulating region.

In an exemplary embodiment of the pixel circuit, the pixel circuit further includes a feedback connection between the second gate and a drain connected to the first gate.

In an exemplary embodiment of the pixel circuit, the pixel circuit further includes a capacitor located between the second gate and the feedback connection to the drain connected to the first gate, wherein the capacitor results in additional gain to the input voltage.

In an exemplary embodiment of the pixel circuit, the pixel circuit further includes row select components configured to receive timing signals for addressing the pixel circuit.

In an exemplary embodiment of the pixel circuit, the row select elements include a row select transistor located between a current supply input and a feedback connection between the second gate and a drain terminal of a sensing element In an exemplary embodiment of the pixel circuit, the row select elements include a row select transistor located between a source terminal of a sensing element and an input bias connection In an exemplary embodiment of the pixel circuit, the readout device comprises a readout transistor, wherein the amplified input voltage is applied to the gate of the readout transistor and the output signal is read out from a source of the readout transistor.

In an exemplary embodiment of the pixel circuit, a first transistor includes the first gate and a second transistor includes the second gate, the first and second transistors being connected in parallel.

In an exemplary embodiment of the pixel circuit, the first transistor has a larger width than the second transistor at least by a factor of two.

In an exemplary embodiment of the pixel circuit, the pixel circuit further comprises a feedback connection between the second gate of the second transistor and a drain of the first transistor; the readout device comprises a readout transistor, wherein the amplified input voltage is applied to a gate of the readout transistor and the output signal is read out from an output of the readout transistor; and the second gate of the second transistor is connected to a node leading to the feedback connection and the gate of the readout transistor.

In an exemplary embodiment of the pixel circuit, the first gate and the second gate comprise a first amplification element, and the pixel circuit further comprises a second amplification element connected between an output of the first amplification element and the readout device; the second amplification element comprising a third gate electrically connected to the output of the first amplification element, and a fourth gate in electrical communication with the third gate, wherein the fourth gate is electrically connected to the readout device.

In an exemplary embodiment of the pixel circuit, the first amplification element and the second amplification element are configured with the same circuit configuration.

Another aspect of the invention is a sensor array. In exemplary embodiments, the sensor array may include a plurality of pixels disposed on a substrate, each pixel including a pixel circuit according to any of the embodiments, row and column driver circuits configured to generate signals that selectively address one or more of the plurality of pixels and for reading out voltages at the sensing electrodes of the addressed pixels, and control electronics configured to control the row and column driver circuits.

Another aspect of the invention is a method of driving a pixel array sensing device comprising a plurality of pixels, with each pixel in the pixel array acting as a sensing element in the sensing device, and each pixel including a pixel circuit comprising: a sensing electrode; a first gate electrically connected to the sensing electrode; a second gate in electrical communication with the first gate via an active region; and a readout device that is electrically connected to the second gate. In exemplary embodiments, the driving method may include the steps of biasing each pixel circuit with a constant input current source; applying timing signals to one or more row selection elements to selectively address one or more of the pixel circuits; perturbing an input voltage to the sensor element in each of the addressed pixel circuits, wherein the input voltage applied to the sensing electrode is amplified between the first gate and the second gate in each of the addressed pixel circuits; and reading out an output signal from the readout device in each of the addressed pixel circuits to perform a sensing operation.

In another exemplary embodiment, the driving method may include the steps of biasing each pixel circuit with a constant input current source, wherein a drain connected to the first gate is configured to receive the input current source; applying timing signals to one or more row selection elements to selectively address one or more of the pixel circuits; perturbing the input current source; and reading out an output signal from the readout device in each of the addressed pixel circuits to perform a sensing operation.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide a sensor array element with in-pixel amplification allowing enhanced low-cost TFT bio-sensor arrays. Such bio-sensor arrays could find application in assays resulting in a pH change, DNA detection (for example qPCR) and surface binding of bio-molecules (for example proteins and DNA sequencing). Arrays based upon this element circuit design could also form part of a lab-on-a-chip system. Applications include healthcare diagnostic testing, material testing, chemical or biochemical material synthesis, proteomics, tools for research in life sciences and forensic science.

What is claimed is:

1. A method of driving a pixel array sensing device comprising a plurality of pixels;
   each pixel in the pixel array acting as a sensing element in the sensing device, and each pixel including a pixel circuit comprising: a sensing electrode; a first gate electrically connected to the sensing electrode; a second gate in electrical communication with the first gate via an active region; and a readout device that is electrically connected to the second gate;
   wherein the sensing electrode, first gate, second gate, and readout device are integrated onto a common substrate;
   the driving method comprising the steps of:
   biasing each pixel circuit with a constant input current source;
   applying timing signals to one or more row selection elements to selectively address one or more of the pixel circuits;
   perturbing an input voltage to the sensor element in each of the addressed pixel circuits, wherein the input voltage applied to the sensing electrode is amplified between the first gate and the second gate in each of the addressed pixel circuits; and
   reading out an output signal from the readout device in each of the addressed pixel circuits to perform a sensing operation.

2. A method of driving a pixel array sensing device comprising a plurality of pixels;
   each pixel in the pixel array acting as a sensing element in the sensing device, and each pixel including a pixel circuit comprising: a sensing electrode; a first gate electrically connected to the sensing electrode; a second gate in electrical communication with the first gate via an active region; and a readout device that is electrically connected to the second gate;
   wherein the sensing electrode, first gate, second gate, and readout device are integrated onto a common substrate;
   the driving method comprising the steps of:
   biasing each pixel circuit with a constant input current source, wherein a drain connected to the first gate is configured to receive the input current source;
   applying timing signals to one or more row selection elements to selectively address one or more of the pixel circuits;
   perturbing the input current source; and
   reading out an output signal from the readout device in each of the addressed pixel circuits to perform a sensing operation.

3. The driving method of claim 1, further comprising connecting the active region to an active region drain and an active region source to form a transistor comprising a channel between the first gate and the second gate.

4. The driving method of claim 1, further comprising connecting the first gate to the sensing electrode by a via connection through an insulating layer and a passivation surface.

5. The driving method of claim 1, wherein:
   the first gate is associated with a first gate capacitance and the second gate is associated with second gate capacitance, and the first gate capacitance is larger than the second gate capacitance; and
   amplification of the input voltage is based on a capacitance ratio of the first gate capacitance to the second gate capacitance.

6. The driving method of claim 1, further comprising a incorporating a feedback connection between the second gate and a drain connected to the first gate.

7. The driving method of claim 6, further comprising connecting a capacitor located between the second gate and the feedback connection to the drain connected to the first gate, wherein the capacitor results in additional gain to the input voltage.

8. The driving method of claim 1, further comprising connecting row select components configured to receive timing signals for addressing the pixel circuit.

9. The driving method of claim 8, wherein the row select elements include a row select transistor located between a current supply input and a feedback connection between the second gate and a drain terminal of a sensing element.

10. The driving method of claim 8, wherein the row select elements include a row select transistor located between a source terminal of a sensing element and an input bias connection.

11. The driving method of claim 1, wherein the readout device comprises a readout transistor, the driving method further comprising applying the amplified input voltage to the gate of the readout transistor and reading the output signal from a source of the readout transistor.

12. The pixel circuit of claim 1, wherein a first transistor includes the first gate and a second transistor includes the second gate, the first and second transistors being connected in parallel.

13. The pixel circuit of claim 12, wherein the first transistor has a larger width than the second transistor at least by a factor of two.

14. The pixel circuit of claim 13, wherein:
   the pixel circuit further comprises a feedback connection between the second gate of the second transistor and a drain of the first transistor;
   the readout device comprises a readout transistor, wherein the amplified input voltage is applied to a gate of the readout transistor and the output signal is read out from an output of the readout transistor; and
   the second gate of the second transistor is connected to a node leading to the feedback connection and the gate of the readout transistor.

15. The pixel circuit of claim 1, wherein the first gate and the second gate comprise a first amplification element, and the pixel circuit further comprises a second amplification element connected between an output of the first amplification element and the readout device;
   the second amplification element comprising a third gate electrically connected to the output of the first amplification element, and a fourth gate in electrical communication with the third gate, wherein the fourth gate is electrically connected to the readout device.

* * * * *